(12) United States Patent
Omori et al.

(10) Patent No.: US 8,231,911 B2
(45) Date of Patent: Jul. 31, 2012

(54) SERUM URIC ACID LEVEL-DECREASING AGENT AND FOOD AND DRINK WITH LABEL TELLING THAT FOOD AND DRINK DECREASE SERUM URIC ACID LEVEL

(75) Inventors: Toshiro Omori, Usa (JP); Hideki Hokazono, Usa (JP)

(73) Assignee: Sanwa Shurui Co., Ltd., Usa-shi (JP)

( * ) Notice: Subject to any disclaimer, the term of this patent is extended or adjusted under 35 U.S.C. 154(b) by 176 days.

(21) Appl. No.: 12/532,034

(22) PCT Filed: Mar. 19, 2008

(86) PCT No.: PCT/JP2008/000657
§ 371 (c)(1),
(2), (4) Date: Feb. 19, 2010

(87) PCT Pub. No.: WO2008/129802
PCT Pub. Date: Oct. 30, 2008

(65) Prior Publication Data
US 2010/0151063 A1    Jun. 17, 2010

(30) Foreign Application Priority Data
Mar. 20, 2007   (JP) .................................. 2007-073231

(51) Int. Cl.
*A01N 65/00*    (2009.01)
(52) U.S. Cl. ..................................................... 424/725
(58) Field of Classification Search .................. None
See application file for complete search history.

(56) References Cited

U.S. PATENT DOCUMENTS

| | | |
|---|---|---|
| 2002/0190759 A1 | 12/2002 | Tour et al. |
| 2005/0281898 A1 | 12/2005 | Sugiyama et al. |
| 2007/0128744 A1 | 6/2007 | Tour et al. |
| 2007/0297216 A1 | 12/2007 | Tour et al. |

FOREIGN PATENT DOCUMENTS

| | | |
|---|---|---|
| JP | 5-238943 A | 9/1993 |
| JP | 2001-258504 A | 9/2001 |
| JP | 2002-121145 A | 4/2002 |
| JP | 2003-38158 A | 2/2003 |
| JP | 2003-252776 A | 9/2003 |
| JP | 3495429 B2 | 2/2004 |
| JP | 2004-238453 A | 8/2004 |
| JP | 2004-359608 A | 12/2004 |
| JP | 2005-507319 A | 3/2005 |
| JP | 2005-281159 A | 10/2005 |
| JP | 2006-1902 A | 1/2006 |
| WO | 2004/112809 A1 | 12/2004 |

OTHER PUBLICATIONS

International Search Report of PCT/JP2008/000657, mailing date Jun. 10, 2008.
Nagao, Akihiko et al., "Inhibition of Xanthime Oxidase by Flavanoids", Biosci. Biotechnol. Biochem., 1999, pp. 1787-1790, vol. 63, No. 10.
Yoshizumi, Kazuma et al.; "The Xanthine Oxidase Inhibitory Activity and Hypouricemia Effect of the Propolis in Rats" Yakugaku Zasshi, The Pharmaceutical Society of Japan, 2005, pp. 315-321, vol. 125, No. 3.

*Primary Examiner* — Michael Meller
(74) *Attorney, Agent, or Firm* — Westerman, Hattori, Daniels & Adrian, LLP

(57) ABSTRACT

The invention is a composition consisting essentially of a component from barley which has been subjected to alcohol fermentation using *Aspergillus kawachii* and which is a residue from a distillation of distilled spirits of the barley and wherein the component from barley is a fraction produced by ion exchange treatment using an aromatic series or methacryl series wherein the component from barley is separated into a solid fraction and a liquid fraction and wherein the liquid fraction is separated out by the ion exchange treatment and wherein the liquid fraction contains the component from barley which decreases a serum uric acid level and wherein the liquid fraction contains crude proteins at 40-60% by weight, polyphenols at 7-12% by weight, polysaccharides at 5-10% by weight, and organic acids at 4-10% by weight.

1 Claim, 1 Drawing Sheet

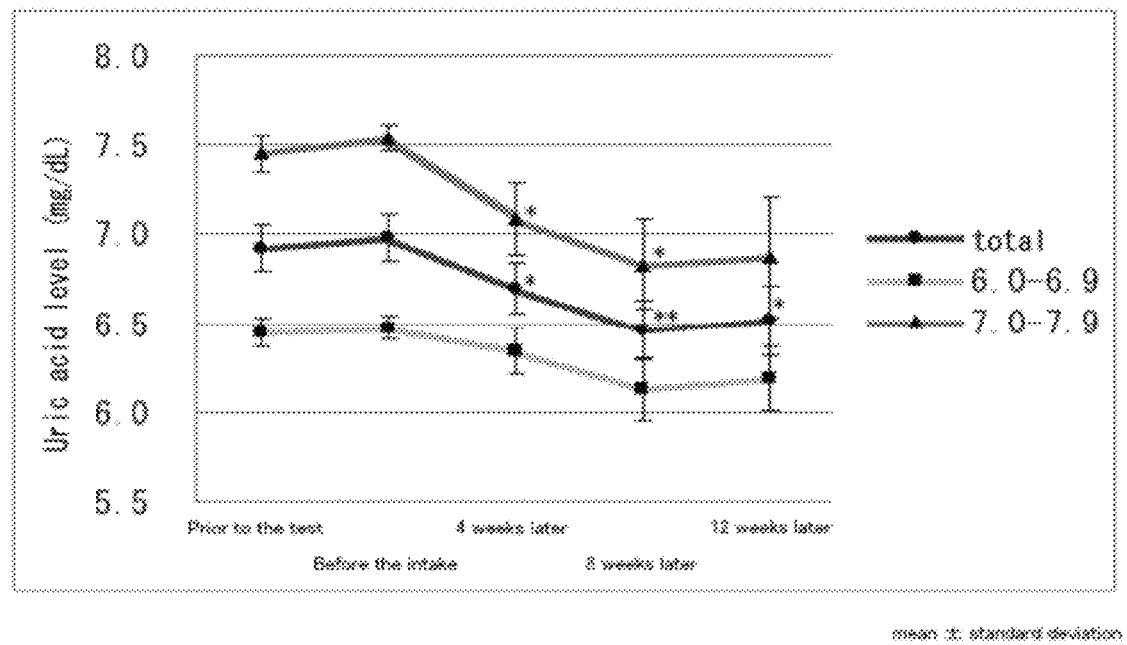

SERUM URIC ACID LEVEL-DECREASING AGENT AND FOOD AND DRINK WITH LABEL TELLING THAT FOOD AND DRINK DECREASE SERUM URIC ACID LEVEL

TECHNICAL FIELD

The present invention relates to a serum uric acid level-decreasing agent containing a component derived from barley subjected to fermentation as the active ingredient, and also relates to a food and a drink with a label telling that the food and the drink are used for the prophylaxis of diseases requiring the decrease of serum uric acid level.

More specifically, the invention relates to a serum uric acid level-decreasing agent for use in the prophylaxis or therapeutic treatment of diseases requiring the decrease of the uric acid level in human sera through the inhibition of uric acid synthesis and/or the promotion of the excretion of uric acid, which contains as the active ingredient a desorbed fraction obtained by subjecting as a raw material a residue from the distillation of distilled spirits from barley as a byproduct in the production of distilled spirits from barley to a separation procedure to a solid fraction and a liquid fraction to obtain the liquid fraction, subjecting the liquid fraction to an adsorption treatment with a synthetic adsorbent to obtain an adsorbed fraction, and then eluting the adsorbed fraction, using an alkali or an organic solvent; a composition containing the serum uric acid level-decreasing agent in a form of a food, a drink or a feed; and a food and a drink with a label telling that the food and the drink are used for the prophylaxis of diseases requiring the decrease of serum uric acid level.

BACKGROUND OF THE INVENTION

Uric acid is a white substance with no taste and no odor, and is produced from purine when cells are decomposed or in the course of energy metabolism. Since higher primates such as human and monkey and a part of fishes and reptiles cannot decompose uric acid, uric acid concentration in the blood gets higher when the synthesis of uric acid is accelerated or the excretion speed of uric acid is decreased in such organisms. Additionally because uric acid is a slightly water-soluble substance, uric acid not dissolvable above the solubility of uric acid in blood or urine is crystallized as sodium urate. Further, the solubility of uric acid is additionally decreased when blood or urine gets acidic or the temperature is lowered. Gout occurring via the deposition of crystallized uric acid in joints or around joints is a disease causing joint disorders, gout knot, urinary calculus and other complications and characteristically involves severe pains.

The Japanese Society of Gout and Nucleic Acid Metabolism defines that a condition at a blood uric acid concentration level exceeding 7.0 mg/dl is hyperuricemia. It is estimated that patients with hyperuricemia at uric acid concentrations of 8.0 mg/dl or more will be 2,000,000 and borderline patients with mild symptoms at uric acid concentrations of 7.0 mg/dl or more will be up to 6,000,000 in Japan. Among the patients with hyperuricemia, the onset of gout is found in about one out of 10. It is estimated currently that there will be 500,000 to 600,000 gout patients in Japan.

Herein, the metabolic syndrome is a syndrome with multiple risk factors and involves the accumulation of organ fats and complications based on accumulated organ fats, such as insulin resistance, abnormal sugar metabolism, abnormal lipid metabolism and hypertension and is therefore a condition readily falling in arteriosclerosis. It is suggested that serum uric acid level is useful as a reference marker to determine the metabolic syndrome. Additionally, it is also indicated that the high level of serum uric acid itself is a risk factor of arteriosclerosis.

As described above, hyperuricemia is not only involved in gout as indicated conventionally but also causes complications of life style-related diseases such as hypertension, hyperlipidemia, abnormal glucose tolerance, and obesity at high frequencies. Hence, attention is now increasingly focused on the prophylaxis and therapeutic treatment of hyperuricemia as a risk factor of cardiovascular diseases and/or a risk marker thereof.

Based on the balance between the generation and excretion of uric acid, hyperuricemia is broadly classified as a uric acid excretion-decreased type (deterioration of the potency of excreting uric acid in urine), excess uric acid generation type (increase of generated uric acid) and a mix type of both of the types described above.

Drugs exist for each disease type of hyperuricemia. For hyperuricemia of the excretion-decreased type, for example, probenecid, bucolome and benzbromarone are used; for hyperuricemia of the excess generation type, allopurinol is used. However, the therapeutic treatment for the decrease of uric acid with these drugs not only requires attention toward adverse actions and drug interactions but also requires deliberate cautions toward the indication thereof to hyperuricemia with none of clinical symptoms such as gout arthritis or gout knot (so-called asymptomatic hyperuricemia). Therefore, a serum uric acid level-decreasing agent from natural origins and without any adverse actions or with relatively less adverse actions is needed.

Regarding active ingredients from natural origins and with an effect on the amelioration of hyperuricemia, patent document 1 describes food compositions containing as the active ingredient dried products and/or extracts of hamamelis and Linonium wrightii O. Kuntze; patent document 2 describes foods or pharmaceutical agents containing as the active ingredient a plant such as meadow sweet, cinnamon, *Lippia triphylla*, *Rhodiola rosea*, *Rhodiola sachalinensis*, *Alpinia galangal*, nutmeg, St. John's wort, and grape, or propolis; patent document 3 describes plants selected from *Origanum vulgare, Mosla chinensis, Elsholtzia ciliate*, lemon balm, rosemary, spearmint, peppermint, winter savory, *Piper betle* and *Carmona retusa*, and/or extracts of such plants.

Further, non-patent document 1 describes that flavonoids existing in various foods and drinks derived from plants have an effect of inhibiting xanthine oxidase; and non-parent reference 2 describes an action of propolis to inhibit xanthine oxidase and an action derived from the action described above to decrease the level of crystalline uric acid.

Still further, patent document 4 describes lactic acid bacteria or yeast with a potency of decomposing purine to exert an action of decreasing serum uric acid level, and also describes a composition containing at least one selected from such microorganisms.

Residues as byproducts at steps of producing for example liquors, Japanese sakes and distilled spirits, such as sake lees as a byproduct at steps of producing Japanese sake and vinegar ("moromi" in Japanese) as a byproduct at steps of producing for example distilled liquors made from rice ("awamorii" in Japanese), have been used traditionally as raw materials of pickles, soups and drinks. Therefore, the safety profiles of the residues as foods have been certified. However, residues from distillation of distilled spirits ("shochu" in Japanese) as derived from distilled spirits from barley ("oh-mugi shochu" in Japanese), distilled spirits from sweet potatoes ("imo shochu" in Japanese) and distilled spirits from rice ("kome shochu" in Japanese) have mostly been disposed so far via for example disposal in oceans and by returning the residues to soil and burning the residues by incineration. The disposal in oceans is an inexpensive disposal method of the residues from distillation of distilled spirits. However, the disposal in oceans is now regulated by rules following the increase of ecological issues, so that the disposal will be absolutely prohibited in future. Furthermore, the procedure of returning the residues to soil disadvantageously pollutes ground water and rivers, while the incineration disposal is disadvantageous in terms of cost and dioxin generation. In view of such problems, currently, an effective utilization of the residues from distillation of distilled spirits has been investigated in diverse fields.

Among others, residues from distillation of distilled spirits from barley are made from barley as a raw material, and barley is a cereal indispensable for humans since the dawn of history and has been familiar as a safe and healthy food as described in traditional Japanese medical books. Accordingly, it is considered that the residues are highly nutritious materials and are highly safe materials, in particular.

From the standpoint of the effective utilization of the residues from distillation of distilled spirits, the present inventors propose in patent document 5 a method for producing a feed from residues from distillation of distilled spirits.

Additionally as inventions of utilizing a residue from distillation of distilled spirits from barley as a byproduct in the production of distilled spirits from barley as a raw material as made by the inventors, patent document 6 describes that a purified concentrate isolated by subjecting a residue from distillation of distilled spirits from barley as a byproduct in the production of distilled spirits from a raw material barley to a separation procedure to a solid fraction and a liquid fraction to obtain the liquid fraction, subjecting the liquid fraction to an absorption treatment with a synthetic adsorbent to obtain the adsorbed fraction, and eluting the adsorbed fraction with an alkali or an organic solvent has an action of suppressing the onset of orotinic acid-inducing fatty liver and/or D-galactosamine-inducing hepatitis; and patent document 7 describes that the fraction obtained from the residue from distillation of distilled spirits from barley in the same manner as in patent document 6 has an exceedingly great anti-oxidant action. Additionally, patent document 8 describes that the fraction obtained from the residue from distillation of distilled spirits from barley in the same manner as in patent document 6 has an exceedingly great pharmacological action of enhancing memory and learning ability.

Patent document 1: JP-A-2000-83862
Patent document 2 JP-A-2002-121145
Patent document 3: JP-A-2003-252776
Patent document 4: JP-A-2005-507319
Patent document 5: Patent No. 3495429
Patent document 6: JP-A-2003-38153
Patent document 7: JP-A-2004-238453
Patent document 8: JP-A-2004-359608
Non-patent document 1: Biosci. Biotechnol. Biochem., 63(10), 1787-1790, 1999
Non-patent document 2: Yakugaku Zasshi (Japanese Journal of Pharmaceutical Medicine), 125(3), 315-321, 2005

DISCLOSURE OF THE INVENTION

Problems that the Invention is to Solve

As described above, patent documents 1 through 3 and non-patent documents 1 and 2 describe active ingredients from natural origins, which have effects of ameliorating hyperuricemia. These references however never describe plants of the family Gramineae including barley. Furthermore, the active ingredients described therein are plants themselves or extracts from plants, without any fermentation process. The action of ameliorating hyperuricemia as exerted by the compositions described in the patent documents 1 through 3 and the non-patent documents 1 and 2 are ascribed to the effect of inhibiting xanthine oxidase as an enzyme to promote the metabolism of xanthine in organisms to uric acid. Hence, the action is used as an action of ameliorating hyperuricemia of "the excess generation type". Further, the principal agent in the composition exerting the action of decreasing serum uric acid level as described in patent document 4 is the microorganism itself having a potency of decomposing purine. Furthermore, the action of ameliorating hyperuricemia as exerted by the composition described in patent document 4 comprises decomposing purine existing in blood as a precursor of uric acid to decrease the absolute amount of the precursor, so that excess generation of uric acid is suppressed. Hence, the action is used as an action of ameliorating hyperuricemia of "the excess generation type".

As described above, it has been identified that components derived from barley subjected to fermentation and residues from distillation of distilled spirits from barley have various physiological activities. However, most of residues from distillation of distilled spirits from barley have been disposed. Some of components derived from barley subjected to fermentation and residues from distillation of distilled spirits from barley have been used as food materials with physiological functions such as an action of suppressing fatty liver, an anti-oxidant action and an action of enhancing memory and learning ability. However, it has never been known so far that components derived from barley subjected to fermentation and residues from distillation of distilled spirits from barley have an action of decreasing uric acid level in human sera.

It is an object of the invention to provide a composition with an action of decreasing uric acid level in human sera from materials having been disposed so far despite no problems in terms of safety, preferably components from barley subjected to fermentation and residues from distillation of distilled spirits from barley, by a simple treatment method suitable for practical industrial-scale production without any complicated purification steps, where the composition is preferably a composition for the prophylaxis or therapeutic treatment of diseases requiring the decrease of serum uric acid level in primates including humans, more specifically a composition in a form selected from the group consisting of food additives, food materials, foods and drinks, pharmaceutical products and quasi-pharmaceutical products, and feeds.

Means for Solving the Problems

So as to solve the problems, the inventors made investigations experimentally. Surprisingly, the inventors found that a desorbed fraction obtained by subjecting the residue from the distillation of distilled spirits from barley to a separation procedure to a solid fraction and a liquid fraction to obtain the liquid fraction (residual solution from distillation of distilled spirits from barley), subjecting the liquid fraction to an adsorption treatment with a synthetic adsorbent to obtain an adsorbed fraction, and then eluting the adsorbed fraction, using an alkali or an organic solvent, had an action of decreasing uric acid level in human sera. The invention has been achieved on the basis of the finding. Specifically, the invention provides a composition with an action of extremely greatly decreasing uric acid level in human sera from a residue from distillation of distilled spirits from barley, as one type of fermentation residues never used actively so far for the purpose of obtaining a food or a pharmaceutical product characteristically decreasing uric acid level in human sera, as well as a method for producing the same.

The invention is summarized as the serum uric acid level-decreasing agent, as described below in (1) through (10).

(1) A serum uric acid level-decreasing agent containing a component from barley subjected to fermentation as the active ingredient.
(2) The serum uric acid level-decreasing agent described in (1), where the component from barley subjected to fermentation is a residue from distillation of distilled spirits from barley.
(3) The serum uric acid level-decreasing agent described in (1) or (2), where the component from barley subjected to fermentation is a liquid fraction (residual solution from distillation of distilled spirits from barley) prepared by subjecting the residue from distillation of distilled spirits from barley to a separation procedure to a solid fraction and the liquid fraction, and/or a composition obtained by fractionating the residual solution from distillation of distilled spirits from barley.
(4) The serum uric acid level-decreasing agent described in (3), where the residual solution from distillation of distilled spirits from barley contains crude proteins at 20 to 40% by weight, polyphenol at 1 to 5% by weight, polysaccharides at 20 to 40% by weight (sugar composition: glucose at 0 to 5% by weight, xylose at 6 to 15% by weight, and arabinose at 5 to 20% by weight), organic acids at 8 to 30% by weight (malic acid at 2 to 6% by weight, citric acid at 5 to 10% by weight, succinic acid at 0 to 4% by weight, lactic acid at 0 to 6% by weight, and acetic acid at 0 to 4% by weight), and free sugars at 0 to 12% by weight (maltose at 0 to 3% by weight, xylose at 0 to 3% by weight, arabinose at 0 to 3% by weight, and glucose at 0 to 3% by weight).
(5) The serum uric acid level-decreasing agent described in (3) or (4), where the composition obtained by fractionating the residual solution from distillation of distilled spirits from barley is an adsorbed fraction with a synthetic adsorbent, where the adsorbed fraction is a desorbed fraction obtained by eluting the adsorbed fraction through an adsorbing treatment of the residual solution from distillation of distilled spirits from barley with the synthetic adsorbent, using an alkali or an organic solvent, or a fraction obtained by treating the desorbed fraction by an ion exchange treatment.
(6) The serum uric acid level-decreasing agent described in (5), where the synthetic adsorbent is one or more synthetic adsorbents selected from the group consisting of synthetic adsorbents of aromatic series, modified aromatic series and methacryl series.
(7) The serum uric acid level-decreasing agent described in (5), where the ion exchange treatment is a cation exchange treatment.
(8) The serum uric acid level-decreasing agent described in (5), (6) or (7), where the adsorbed fraction with the synthetic adsorbent contains crude proteins at 40 to 60% by weight, polyphenol at 7 to 12% by weight, polysaccharides at 5 to 10% by weight (sugar composition: glucose at 0 to 2% by weight, xylose at 3 to 5% by weight, and arabinose at 2 to 5% by weight), organic acids at 4 to 10% by weight (malic acid at 1 to 3% by weight, citric acid at 2 to 4% by weight, succinic acid at 0 to 1% by weight, lactic acid at 0 to 6% by weight, and acetic acid at 0 to 1% by weight), and free sugars at 0 to 2% by weight (maltose at 0 to 1% by weight, xylose at 0 to 1% by weight, arabinose at 0 to 1% by weight, and glucose at 0 to 1% by weight).
(9) The serum uric acid level-decreasing agent described in any of (1) through (8), which is a pharmaceutical agent for the prophylaxis or therapeutic treatment of diseases requiring the decrease of serum uric acid level.
(10) The serum uric acid level-decreasing agent described in (9), where the diseases requiring the decrease of serum uric acid level are gout arthritis, gout knot, urinary calculus, gout kidney, and/or life style-related diseases and the metabolic syndrome with a complication of hyperuricemia, such as hypertension, hyperlipidemia, obesity, abnormal glucose tolerance, diabetes mellitus or ischemic cardiac diseases.

The invention is also summarized as the composition described in (11).

(11) A composition in a form of foods or drinks, pharmaceutical products or quasi-pharmaceutical products or feeds, the composition containing the serum uric acid level-decreasing agent described in any of (1) through (10).

The invention is additionally summarized as described below in (12) through (21).

(12) A food and a drink with a label telling that the food and the drink contain a component from barley subjected to fermentation and are used for the prophylaxis of diseases requiring the decrease of serum uric acid level.
(13) The food and the drink described in (12), where the diseases requiring the decrease of serum uric acid level are gout arthritis, gout knot, urinary calculus, gout kidney, and/or life style-related diseases and the metabolic syndrome with a complication of hyperuricemia, such as hypertension, hyperlipidemia, obesity, abnormal glucose tolerance, diabetes mellitus or ischemic cardiac diseases.
(14) The food and the drink described in (12) or (13), which are a functional food and a functional drink, a food and a drink as nutritious supplements or a healthy food and a healthy drink, for decreasing serum uric acid level.
(15) The food and the drink described in any of (12) through (14), where the component from barley subjected to fermentation is a residue from distillation of distilled spirits from barley.
(16) The food and the drink described in any of (12) through (15), where the component from barley subjected to fermentation is a liquid fraction (residual solution from distillation of distilled spirits from barley) obtained by subjecting the residue from distillation of distilled spirits from barley to a separation procedure to a solid fraction and the liquid fraction and/or a composition obtained by fractionating the residual solution from distillation of distilled spirits from barley.
(17) The food and the drink described in (16), where the residual solution from distillation of distilled spirits from barley contains crude proteins at 20 to 40% by weight, polyphenol at 1 to 5% by weight, polysaccharides at 20 to 40% by weight (sugar composition: glucose at 0 to 5% by weight, xylose at 6 to 15% by weight, and arabinose at 5 to 20% by weight), organic acids at 8 to 30% by weight (malic acid at 2 to 6% by weight, citric acid at 5 to 10% by weight, succinic acid at 0 to 4% by weight, lactic acid at 0 to 6% by weight, and acetic acid at 0 to 4% by weight), and free sugars at 0 to 12% by weight (maltose at 0 to 3% by weight, xylose at 0 to 3% by weight, arabinose at 0 to 3% by weight, and glucose at 0 to 3% by weight).
(18) The food or the drink described in (17), where the composition obtained by fractionating the residual solution from distillation of distilled spirits from barley is an adsorbed fraction with a synthetic adsorbent, a desorbed fraction obtained by eluting the adsorbed fraction through an adsorbing treatment of the residual solution from distillation of distilled spirits from barley with the synthetic adsorbent, using an alkali or an organic solvent, or a fraction obtained by treating the desorbed fraction obtained by eluting the adsorbed fraction through the adsorbing treatment of the residual solution from distillation of distilled spirits from barley with the synthetic adsorbent, using an alkali or an organic solvent, by an ion exchange treatment.

(19) The food and the drink described in (18), where the synthetic adsorbent is one or more synthetic adsorbents selected from the group consisting of synthetic adsorbents of aromatic series, modified aromatic series or methacryl series.

(20) The food and the drink described in (18), where the ion exchange treatment is a cation exchange treatment.

(21) The food and the drink described in (18), (19) or (20), where the adsorbed fraction with the synthetic adsorbent contains crude proteins at 40 to 60% by weight, polyphenol at 7 to 12% by weight, polysaccharides at 5 to 10% by weight (sugar composition: glucose at 0 to 2% by weight, xylose at 3 to 5% by weight, and arabinose at 2 to 5% by weight), organic acids at 4 to 10% by weight (malic acid at 1 to 3% by weight, citric acid at 2 to 4% by weight, succinic acid at 0 to 1% by weight, lactic acid at 0 to 6% by weight, and acetic acid at 0 to 1% by weight), and free sugars at 0 to 2% by weight (maltose at 0 to 1% by weight, xylose at 0 to 1% by weight, arabinose at 0 to 1% by weight, and glucose at 0 to 1% by weight).

Advantages of the Invention

In accordance with the invention, there are provided a serum uric acid level-decreasing agent with an action of decreasing uric acid level inhuman sera from materials readily available inexpensively or materials having been disposed so far, with no problems in terms of safety, preferably components from barley subjected to fermentation and/or residues from distillation of distilled spirits from barley, by a simple treatment method suitable for practical industrial-scale production without any complicated purification steps, and a food and a drink with a label telling that the food and the drink can decrease serum uric acid level, which are preferably a serum uric acid level-decreasing agent for the prophylaxis or therapeutic treatment of diseases requiring the decrease of serum uric acid level in primates including humans, compositions containing the same in forms of foods and drinks, pharmaceutical products and quasi-pharmaceutical products or feeds, and foods and drinks with a label telling that the foods and the drinks are used for the prophylaxis of diseases requiring the decrease of serum uric acid level.

The finding described in accordance with the invention that the component from barley subjected to fermentation and/or the residue from distillation of distilled spirits from barley has an action of decreasing uric acid level in human sera is a novel fact absolutely never found so far, which can create a novel application that the component from barley subjected to fermentation and/or the residue from distillation of distilled spirits from barley can be used as pharmaceutical products or quasi-pharmaceutical products for the prophylaxis or therapeutic treatment of diseases requiring the decrease of uric acid level in human sera or can be used as a food and a drink with a label telling that the food and the drink can be used for the prophylaxis of diseases requiring the decrease of serum uric acid level.

BRIEF DESCRIPTION OF THE DRAWING

FIG. 1 is a view describing the results of a test in Example 2 for examining the action of decreasing uric acid level in human sera.

BEST MODE FOR CARRYING OUT THE INVENTION

The composition for decreasing human uric acid level in accordance with the invention (a serum uric acid level-decreasing agent, a composition containing the same or a food and a drink with a label telling that the food and the drink can decrease serum uric acid level) characteristically contains a component from barley subjected to fermentation as the active ingredient for the action of decreasing serum uric acid level. The substance with the action of decreasing serum uric acid level as contained in the component from barley subjected to fermentation is preferably a substance contained in the residue from distillation of distilled spirits from barley. The substance contained in the residue from distillation of distilled spirits from barley includes one or more compositions selected from a liquid fraction (residual solution from distillation of distilled spirits from barley) obtained by subjecting the residue from distillation of distilled spirits from barley to a separation procedure to a solid fraction and the liquid fraction, a desorbed fraction obtained by subjecting the liquid fraction to an adsorbing treatment with a synthetic adsorbent to obtain an adsorbed fraction and then eluting the adsorbed fraction, using an alkali or organic solvent, and a fraction obtained by an ion exchange treatment of the desorbed fraction.

The composition with an action of decreasing human serum uric acid level in accordance with the invention (serum uric acid level-decreasing agent, a composition containing the same or a food and a drink with a label telling the food and the drink can decrease serum uric acid level) is obtained from materials readily available inexpensively and/or materials having been disposed so far, with not any problematic safety profile, preferably a component from barley subjected to fermentation and/or a residue from distillation of distilled spirits from barley, by a simple treatment method suitable for practical industrial-scale production without any complicated purification steps. The composition is applied biologically by using the composition in foods and drinks, pharmaceutical products and feeds, so that an excellent action of decreasing serum uric acid level can be expected. The functional composition of the invention contains a naturally occurring active ingredient with an action of decreasing serum uric acid level. Via the application of the action of decreasing serum uric acid level on the basis of the active ingredient, for example, a safe therapeutic method of gout can be led. The action of decreasing serum uric acid level has an effect on the prophylaxis and safe therapeutic treatment of not only gout but also disorders of joint functions, gout knot, arteriosclerosis, cardiac diseases and other various diseases.

Specifically, the composition for decreasing serum uric acid level in accordance with the invention (the serum uric acid level-decreasing agent, a composition containing the same or a food and a drink with a label telling that the food and the drink can decrease serum uric acid level) is a composition for the prophylaxis or therapeutic treatment of diseases requiring the decrease of serum uric acid level. Any disease in which a high concentration of serum uric acid level is mainly involved in the occurrence of the symptoms may be the subject as the diseases requiring the decrease of serum uric acid level. Thus, the diseases requiring the decrease of serum uric acid level include diseases caused by abnormal elevation of serum uric acid concentration, such as symptoms due to the deposition of crystallized uric acid in joints or around joints and symptoms with complications of plural life style-related diseases induced at conditions with the metabolic syndrome. More specifically, the diseases are for example gout arthritis, gout knot, urinary calculus, gout kidney and/or life style-related diseases and the metabolic syndrome with a complication of hyperuricemia, including for example hypertension, hyperlipidemia, obesity, abnormal glucose tolerance, diabetes mellitus or ischemic cardiac diseases. However, the diseases are not limited to them. In accordance with the invention, preferably, the diseases requiring the decrease of serum uric acid level are gout or arteriosclerosis as targets.

The action of decreasing serum uric acid level in humans as exerted by the serum uric acid level-decreasing agent in accordance with the invention can be verified at a test, where the composition of the invention is administered over 12-week daily life under doctor's controls to determine whether or not the serum uric acid level is decreased compared with the start of the test.

By carrying out the test in normal borderline subjects at a serum uric acid level of 6.0 mg/dL or more to less than 7.0 mg/dL at the test start and borderline subjects with mild symptoms at a serum uric acid level of 7.0 mg/dL or more to less than 8.0 mg/dL at the test start, the prophylactic effect and therapeutic effect for a disease requiring the decrease of serum uric acid level can be determined. The uric acid concentration in human sera can be assayed for example by the uricase-peroxidase method (Clinical Chemistry, Vol. 17, p. 1154).

Accordingly, a material containing the component from barley subjected to fermentation can be provided as a food and a drink with a label telling that the food and the drink can be used for the prophylaxis of diseases requiring the decrease of serum uric acid level.

The barley as the subject for fermentation in accordance with the invention may be any of kawa-barley (hulled barley) and hadaka-barley (hulless barley) or may be any of nijyo-barley (two-row barley) and rokujyo-barley (six-row barley). Additionally, the barley may be colored barley with a dye deposited on the surface of the husk. The barley may be in any form with no specific limitation. Preferably, the whole grain such as unpolished barley is used. Further, barley may be treated by treatments including roasting, milling and compression.

In fermenting barley, the microorganism at production steps of distilled spirits from barley and at related production steps of a residue from distillation of distilled spirits from barley may be any microorganism with no specific limitation. As such, koji (fungi), yeast, lactic acid bacteria or natto bacteria may be used.

Malted barley for use in obtaining distilled spirits from barley and a residue from distillation of distilled spirits from barley may be produced under routine conditions for general production of distilled spirits from barley. The koji strain for use is preferably *Aspergillus kawachii* for general use in producing distilled spirits from barley. Otherwise, koji(fungi) strains of the genus *Aspergillus* such as *Aspergillus awamorii* for use in "awamori" production and *Aspergillus oryzae* for use in Japanese sakes may also be used. As the yeast for use in obtaining distilled spirits from barley and a residue from distillation of distilled spirits from barley, further, various yeast species for brewing distilled spirits may be used, which are generally used in producing distilled spirits.

The method for obtaining a residual solution from distillation of distilled spirits from barley from the residue from distillation of distilled spirits from barley includes a method for obtaining a liquid fraction via a solid-liquid separation treatment by one or more methods selected from pressing treatments of screw press type and roller press type, centrifugation treatment with a centrifuge of decanter type, or filtration treatment with a filtration apparatus with diatomaceous earth, a ceramic filtration apparatus, or a pressurized squeezer and the like.

As the synthetic adsorbent for use in the treatment with such synthetic adsorbent for the purpose of adsorbing and isolating the component with an action of decreasing serum uric acid level as contained in the residual solution from distillation of distilled spirits from barley, synthetic adsorbents of aromatic series, modified aromatic series, or methacryl series may be used. Preferable specific examples of such synthetic adsorbent includes aromatic-series (also referred to as styrene series) synthetic adsorbents, such as Amberlite XAD-4, Amberlite XAD-16, Amberlite XAD-1180 and Amberlite XAD-2000 manufactured by Rohm and Haas and Sepabeads SP 850 and Dia-ion HP20 manufactured by Mitsubishi Chemical Co., Ltd.; methacryl-series (also referred to as acrylic series) synthetic adsorbents such as Amberlite XAD-7 manufactured by Rohm and Haas and Dia-ion HP2 MG manufactured by Mitsubishi Chemical Co., Ltd.; and synthetic adsorbents of modified aromatic series, such as Sepabeads SP207 manufactured by Mitsubishi Chemical Co., Ltd.

The component with an action of decreasing serum uric acid level as adsorbed on such synthetic adsorbents may be eluted with an organic solvent or an alkali. Preferable specific examples of the organic solvent include ethanol and isopropanol. Preferable specific examples of the alkali include sodium hydroxide and potassium hydroxide. Because the adsorbed fraction eluted from the synthetic adsorbents by using such alkali contains cations such as sodium ion and potassium ion, the adsorbed fraction can additionally be subjected to an ion exchange treatment. Such ion exchange treatment may be done by using a cation exchange resin and the like. Preferable specific examples of the cation exchange resin include strongly acidic cation exchange resins IR-120, IR-120B, and Amberlite 2000CT and poorly acidic cation exchange resins such as IRC50 and IRC 76 as manufactured by Rohm and Haas; and strongly acidic cation exchange resins such as Dia-ion SK 1B, SK 104, and PK 208 and poorly acidic cation exchange resins such as WK10 and WK 40 as manufactured by Mitsubishi Chemical Co., Ltd. The adsorbed fraction eluted from the synthetic adsorbents by using the alkali may be subjected to a neutralization treatment by means of an inorganic acid or organic acid such as hydrochloric acid, acetic acid and citric acid. The adsorbed fraction after the neutralization treatment may additionally be subjected to a desalting treatment by using the cation exchange resins.

The composition with an action of decreasing serum uric acid level as obtained by subjecting barley to fermentation includes for example one or more compositions selected from the group consisting of a residue from distillation of distilled spirits from barley, a residual solution from distillation of distilled spirits from barley, a desorbed fraction obtained by eluting the adsorbed fraction from the adsorption treatment of the residual solution from distillation of distilled spirits from barley by means of a synthetic adsorbent, by using an alkali or an organic solvent, and a fraction obtained by treating the desorbed fraction with an ion exchange treatment.

Herein, these fractions may be used as they are in liquid or slurry, when these fractions are applied as food additives, food materials, foods and drinks, pharmaceutical products and quasi-pharmaceutical products, and feeds with an action of decreasing serum uric acid level. Otherwise, the fractions may be dried as they are or after excipients such as dextrin are added to the fractions.

In another mode, the residual solution from distillation of distilled spirits from barley is used in a culture medium for culturing lactic acid bacteria and natto bacteria, and then, the resulting liquid culture is freeze-dried for use.

The lactic acid bacteria for the use described above preferably include but are not limited to lactic acid bacteria belonging to *Lactococcus lactis* subsp. Lactis. Specifically, the lactic acid bacteria preferably include *Lactococcus lactis* NCD0497, *Lactococcus lactis* NIZO R5, *Lactococcus lactis* ATCC 7962 and *Lactococcus lactis* ATCC 11454, *Lactococcus lactis* NIZO 22186, *Lactococcus lactis* NRRL-B-18583, *Lactococcus lactis* NCFB 2118, *Lactococcus lactis* NCFB 2054, *Lactococcus lactis* NIZO N9, *Lactococcus lactis* NIZO 221186, *Lactococcus lactis* 10-1 (JCM 7638), *Lactococcus lactis* subsp. Lactis A. Ishizaki Chizuka (JCM 11180), *Lactococcus lactis* subsp. Lactis A. Ishizaki Yasaka 5B (JCM 11181), *Lactococcus lactis* subsp. Lactis A. Ishizaki Yasaka 7B (JCM 11182), *Lactococcus lactis* subsp. Lactis A. Ishizaki Yasaka 8B (JCM 11183), and *Lactococcus lactis* subsp. Lactis A. Ishizaki Yasaka 9B (JCM 11184).

The natto bacteria for the use described above include for example but are not limited to bacteria of the Miyagino strain as a commercially available natto strain of *Bacillus subtilis*.

The serum uric acid level-decreasing agent containing one or more selected from the group consisting of the component from barley subjected to fermentation, a residue from distillation of distilled spirits from barley, a residual solution from distillation of distilled spirits from barley, a desorbed fraction obtained by eluting the adsorbed fraction from the adsorption treatment of the residual solution from distillation of distilled spirits from barley by means of a synthetic adsorbent, using an alkali or an organic solvent, and a fraction obtained by treating the desorbed fraction with an ion exchange treatment can be provided in a form selected from the group consisting of food additives, food materials, foods and drinks, pharmaceutical products and quasi-pharmaceutical products, and feeds containing the serum uric acid level-decreasing agent for decreasing serum uric acid level. By actively utilizing the functions of the composition, healthy foods and drinks, foods as nutritious foods and drinks for patients, and feeds for feeding animals such as pets could be developed. In other words, the foods and drinks are functional foods, foods as nutritious supplements or healthy foods and drinks for decreasing serum uric acid level. The feeds are pet feeds for decreasing serum uric acid level.

Further, foods and drinks containing one or more selected from the group consisting of the component from barley subjected to fermentation, a residue from distillation of distilled spirits from barley, a residual solution from distillation of distilled spirits from barley, a desorbed fraction obtained by eluting the adsorbed fraction from the adsorption treatment of the residual solution from distillation of distilled spirits from barley by means of a synthetic adsorbent, using an alkali or an organic solvent, and a fraction obtained by treating the desorbed fraction with an ion exchange treatment are provided as foods and drinks with a label telling that the foods and the drinks are used for the prophylaxis of diseases requiring the decrease of serum uric acid level.

Specifically, a food material containing one or more selected from the group consisting of the component from barley subjected to fermentation, a residue from distillation of distilled spirits from barley, a residual solution from distillation of distilled spirits from barley, a desorbed fraction obtained by eluting the adsorbed fraction from the adsorption treatment of the residual solution from distillation of distilled spirits from barley by means of a synthetic adsorbent, using an alkali or an organic solvent, and a fraction obtained by treating the desorbed fraction with an ion exchange treatment can be used in any form of food forms, drink forms or feed forms.

In case that the function of the composition for decreasing serum uric acid level in accordance with the invention is to be actively used, the content thereof is appropriately adjusted, depending on the intended level of the function, the mode for use, the amount thereof used and the like, but is never limited specifically. For example, the content thereof is 0.001 to 100% by mass. The composition for decreasing serum uric acid level can be used for humans and additionally for foods and drinks, pharmaceutical products and feeds. The composition can be blended in oral products according to general methods and can be used in various fields such as seasonings, food additives, food materials, foods and drinks, healthy foods and drinks, pharmaceutical products and feeds. In case that the composition is blended in foods and drinks, the resulting foods and drinks are foods and drinks for therapeutically treating or preventing diseases requiring the decrease of serum uric acid level. In terms of the effect such as an effect of prophylaxis, it is expected that the composition will be used as healthy foods, nutritious foods and the like. Additionally, the composition will be used in pet feeds. As described above, the composition containing one or more selected from a component from barley subjected to fermentation, a residue from distillation of distilled spirits from barley, a residual solution from distillation of distilled spirits from barley, a desorbed fraction obtained by eluting the adsorbed fraction from the adsorption treatment of the residual solution from distillation of distilled spirits from barley by means of a synthetic adsorbent, using an alkali or an organic solvent, and a fraction obtained by treating the desorbed fraction with an ion exchange treatment is used for humans or additionally in foods and drinks, pharmaceutical products and feeds, so that the composition can exert the effect of preventing or therapeutically treating diseases requiring the decrease of serum uric acid level. Furthermore, the composition can readily be obtained from materials having been disposed so far, such as outer barley husk, barley bran, residues from distillation of distilled spirits from barley, and residual solutions from distillation of distilled spirits from barley. In view of cost and in terms of effective utilization of resources, therefore, the composition is preferable.

In case that the inventive composition is to be used in foods, the composition is used as it is or is prepared in forms such dilutions with oils and the like, diet forms in emulsion and forms with addition of carries routinely used in food industries.

The diet forms in emulsion may be prepared by adding the composition to an oil phase, further adding a liquid fat such as glycerin fatty acid ester, sorbitan fatty acid ester, sucrose fatty acid ester, glycerol, dextrin, rapeseed oil, soybean oil and corn oil, and then adding to an aqueous phase, L-ascorbic acid or esters thereof or salts thereof, gum materials for example locust bean gum, gum Arabic or gelatin, flavonoids or polyphenols for example hesperidine, rutin, quercetin, catechin, and thianidine or mixtures thereof, and emulsifying the resulting mixture.

The forms of the drinks are non-alcoholic drinks or alcoholic drinks. The non-alcoholic drinks include for example carbonate drinks, non-carbonate drinks such as refreshing drinks, fruit juice drinks, and nectar drinks, sport drinks, tea, coffee and cocoa. The alcoholic drinks include for example alcohol drinks in general food forms such as spirits, liquors, distilled spirits diluted with carbonate drinks ("chew-high" in Japanese), fruit liquors, beer, sparkling liquors, and medical wines or liquors.

The drinks and foods specifically include for example those described below: western-style confectionaries (custard pudding, jelly, gummy candies, candies, drops, caramels, chewing gum, chocolate, pastry, butter cream, custard cream, chew a la cream, hot cake, bread, potato chips, fried potato, pop corn, biscuit, cracker, pie, sponge cake, castella, waffle, cake, doughnut, biscuit, cookies, rice cracker, okaki (small rice cracker), sweet rice cracker, bun with bean-jam filling, and candies), dried noodle products (macaroni, pasta), egg products (mayonnaise, fresh cream), drinks (functional drinks, lactic acid drinks, sour milk beverages, concentrated milk drinks, fruit juice drinks, drinks with no fruit juice, flesh drinks, clear carbonate drinks, carbonate drinks with fruit juice, fruit-colored carbonate drinks), favorites (green tea, tea, instant coffee, cocoa, canned coffee drinks), milk products (ice cream, yoghurt, milks for coffee, butter, butter sauce, cheese, fermented milk, processed milk), pastes (marmalade, jam, flower paste, peanut paste, fruit paste, fruit dipped in syrups), meat products (ham, sausage, bacon, dry sausage, beef jerky, lard), products of fishes and shell fishes (fish ham, fish sausage, boiled fish cake, tube-shaped fish paste cake, cake of pounded fish, dry fishes, dried bonito, dried mackerel, dried small sardines, sea urchin, salted squid guts, dried squid, dried fish after raw fish is seasoned with soy sauce and mirin, dried shell fish, smoked products of salmon, etc.), boiled fishes, vegetables, etc. after seasoning with soy sauce and other seasonings (small fishes, shell fishes, edible wild plants, mushroom, seaweed), curries (instant curry, retort curry, canned curry), seasonings (miso paste, powdered miso paste, soy sauce, powdered soy sauce, moromi, fermented fish sauce, Worcestershire sauce, ketchup, oyster sauce, solid bouillon, gravy for boiled meat, curry roux, stew sauce, soup seasonings, Japanese soup seasonings, paste, instant soup, sprinkles for rice, dressings, salad oil), fried products (soybean curb (tofu) fried in oil, confectioneries fried in oil, instant Chinese noodle), soybean milk, margarine, and shortening.

The drinks and foods described above can be produced by blending and processing the composition with raw materials for general foods according to general methods.

The amount of the composition blended in the drinks and foods is variable depending on the form of the food, so the amount is not specifically limited. Generally, however, the amount is at 0.001 to 30%, preferably.

The foods and the drinks may also be used as functional foods, foods as nutritious supplements, or healthy foods. The form is not specifically limited. For example, production examples of such foods are proteins such as milk proteins highly nutritious in good amino acid balance, soybean protein and egg albumin, decompositions products thereof, oligopeptides from egg white, and decomposed soybean products and additionally include mixtures of single amino acids. Further, the foods and drinks may also be used in forms such as soft capsules and tablets.

Examples of foods as nutritious supplements or functional foods include processed forms such as liquid diets, semi-digested nutritious diets, nutritious element diets, drinks, capsules and enteral diets, which are in blend with for example sugars, fat, trace elements, vitamins, emulsifiers and flavor. So as to improve nutrition balance and flavor, the individual foods for example foods and drinks such as sport drinks and nutritious drinks may be blended with nutritious additives such as amino acids, vitamins, and minerals, sweeteners, spices, flavor and dyes.

So as to stabilize the composition of the invention, antioxidant agents, for example, tocopherol, L-ascorbic acid, BHA and rosemary extract may be used in combination according to general methods.

The composition of the invention may be applied to feeds for pets. For example, the composition may be blended in feeds for primate pets. The feeds themselves may be prepared according to general methods.

The methods for producing individual compositions from barley and the component from barley subjected to fermentation as raw materials and the action of the compositions to decrease human serum uric acid level will now be described below. However, the scope of the invention is not limited to the following examples.

EXAMPLE 1

<Production of Distilled Spirits from Barley and Residue from the Distillation of Distilled Spirits from Barley>

Barley absorbed water to 40 w/w %, for steaming for 40 minutes. Then, the steamed barley was cooled to 40° C., to which seed koji (*Aspergillus kawachii*) of 1 kg per 1 ton of barley was inoculated and retained at 38° C. and 95% RH for 24 hours and at 32° C. and 92% RH for 20 hours, to produce malted barley. At the first charge, 3.6 kiloliters of water and 1 kg (wet weight) of the cultured cells of the yeast for distilled spirits as yeast were charged in the malted barley (3 tons as barley) produced by the method described above, to obtain a first moromi; the resulting first moromi was subjected to fermentation for 5 days (the first-step fermentation). At the second charge, then, 11.4 kiloliters of water and the steamed barley (7 tons as barley) produced by the method described above were added to the first moromi after completion of the first-step fermentation, for fermentation for 11 days (the second-step fermentation). The fermentation temperature was 25° C. for both the first and second charges. The second moromi after completion of the second-step fermentation was subjected to single distillation using a pot still, to obtain 10 kiloliters of distilled spirits from barley and 15 kiloliters of a residue from distillation of distilled spirits from barley.

<Recovery of Residual Solution from the Distillation of Distilled Spirits from Barley and Adsorbed Fraction with Synthetic Adsorbent as Derived from Residue from the Distillation of Distilled Spirits from Barley>

[Residual Solution from the Distillation of Distilled Spirits from Barley]

The residue from the distillation of distilled spirits from barley was centrifuged under conditions of 8,000 rpm for 10 minutes, to obtain a residual solution from the distillation of distilled spirits from barley (A).

[Adsorbed Fraction with Synthetic Adsorbent]

25 liters of the resulting residual solution from the distillation of distilled spirits from barley (A) and 10 liters of deionized water were treated in this order in a column (resin volume of 10 liters) filled with a synthetic adsorbent Amberlite XAD-16 manufactured by Rohm and Haas. By putting 10 liters of a 1 wt/vol % sodium hydroxide solution and 10 liters of deionized water in this order in contact with the synthetic adsorbent in the column, 20 liters of an eluted solution containing an adsorbed fraction with adsorptivity to the synthetic adsorbent in the column were obtained. By putting 20 liters of the eluted solution in contact with a column (resin volume of 10 liters) filled with a strongly acidic cation exchange resin IR-120B manufactured by Rohm and Haas followed by freeze-drying, 270 g of a freeze-dried product (B) of the adsorbed fraction was obtained, from which sodium ion had preliminarily been removed.

<Analysis of Composition of Adsorbed Fraction with Synthetic Adsorbent>

The composition of the adsorbed fraction with the synthetic adsorbent was analyzed. Specifically, the "production of distilled spirits from barley and residue from the distillation of distilled spirits from barley" was carried out plural times, to prepare plural residues from the distillation of distilled spirits from barley with different lot numbers. In the same manner for the "recovery of residual solution from the distillation of distilled spirits from barley and adsorbed fraction with synthetic adsorbent", the individual residues from the distillation of distilled spirits from barley were centrifuged to obtain residual solutions from the distillation of distilled spirits from barley. Additionally, liters of each of the residual solutions from the distillation of distilled spirits from barley and 10 liters of deionized water in this order were in contact with a column (resin volume of 10 liters) filled with a synthetic adsorbent Amberlite XAD-16 manufactured by Rohm and Haas, to elute adsorbed fractions adsorbed in the column. In such manner, plural analytical samples were prepared. Protein, sugar composition, polyphenol and organic acid composition of the individual analytical samples comprising the residual solutions from the distillation of distilled spirits from barley or the adsorbed fractions with the synthetic adsorbent were analyzed. Protein was assayed by the Kjeldahl method; the sugar composition was assayed by HPLC via hydrochloric acid hydrolysis; polyphenol was assayed by Folin-Ciocalteu method; and the organic acid composition was assayed by HPLC.

[Residual Solution from the Distillation of Distilled Spirits from Barley]

It was shown that the residual solutions from the distillation of distilled spirits from barley contained crude proteins at 20 to 40% by weight, polyphenol at 1 to 5% by weight, polysaccharides at 20 to 40% by weight (sugar composition: glucose at 0 to 5% by weight, xylose at 6 to 15% by weight, and arabinose at 5 to 20% by weight), organic acids at 8 to 30% by weight (malic acid at 2 to 6% by weight, citric acid at 5 to 10% by weight, succinic acid at 0 to 4% by weight, lactic acid at 0 to 6% by weight, and acetic acid at 0 to 4% by weight), and free sugars at 0 to 12% by weight (maltose at 0 to 3% by weight, xylose at 0 to 3% by weight, arabinose at 0 to 3% by weight, and glucose at 0 to 3% by weight).

[Adsorbed Fractions with Synthetic Adsorbent]

It was shown that the adsorbed fractions with the synthetic adsorbent contained crude proteins at 40 to 60% by weight, polyphenol at 7 to 12% by weight, polysaccharides at 5 to 10% by weight (sugar composition: glucose at 0 to 2% by weight, xylose at 3 to 5% by weight, and arabinose at 2 to 5% by weight), organic acids at 4 to 10% by weight (malic acid at 1 to 3% by weight, citric acid at 2 to 4% by weight, succinic acid at 0 to 1% by weight, lactic acid at 0 to 6% by weight, and acetic acid at 0 to 1% by weight), and free sugars at 0 to 2% by weight (maltose at 0 to 1% by weight, xylose at 0 to 1% by weight, arabinose at 0 to 1% by weight, and glucose at 0 to 1% by weight). Furthermore by using a synthetic adsorbent except the synthetic adsorbent XAD-16 for the procedures for preparing the aforementioned analytical samples, analytical samples were prepared, comprising adsorbed fractions with the synthetic adsorbent from the individual plural types of the liquid fractions, namely the residual solutions from the distillation of distilled spirits from barley; in the same manner as described above, the resulting analytical samples were analyzed, to obtain results substantially identical to the results obtained by using Amberlite XAD-16.

EXAMPLE 2

Test Example 1

Test for the Examination of the Action of Decreasing Human Serum Uric Acid Level The residual solution from the distillation of distilled spirits from barley (A) and the freeze-dried product (B) of the adsorbed fraction as obtained in Example 1 were subjected to the following test for the examination of the action of decreasing serum uric acid level, to evaluate the action thereof in humans.

<Subjects for the Test for the Examination>

Subjects satisfying the following three criteria under doctor's observation were enrolled in the test for the examination of the action of decreasing serum uric acid level in Example 2.

(I) Criteria for Subject Selection
1) Normal males of age 20 years old to less than 65 years old, who satisfy the following condition 2) or 3).
2) Males at serum uric acid levels of 6.0 mg/dL or more to less than 7.0 mg/dL prior to the test and at the examination before the intake (normal borderline zone).
3) Males at serum uric acid levels of 7.0 mg/dL or more to less than 8.0 mg/dL prior to the test and at the examination before the intake (borderline zone with mild symptoms).

(II) Criteria for Excluding Subjects
1) Males with the onset of gout symptoms.
2) Males receiving a prescription of pharmaceutical products (including diuretics) with possible influence on uric acid level or males routinely given the pharmaceutical products.
3) Males routinely ingesting healthy foods specified by rules in Japan and healthy foods, in relation with uric acid levels.
4) Males executing kinesitherapy for the purpose of therapeutically treating hyperuricemia (gout).
5) Males daily ingesting foods supplemented with the components involved in the test.
6) Males with histories of chronic renal impairment, cirrhosis, diabetes mellitus, and other severe diseases.
7) Males suspected of chronic or acute infections.
8) Males in the therapeutic treatment of migraine headache.
9) Males with histories of abnormalities in laboratory values and heart-lung functions, so that the males are found to be inappropriate for test enrollment.
10) Males whose laboratory values or physical examination values before the intake are far outside the standard ranges.
11) Males with urine protein of + or more and with positive urine creatinine or males with urine protein of 2+ or more.
12) Males with possible onset of allergy in relation with the test (foods, drugs, metals).
13) Males enrolled in other clinical tests during examinations prior to the test.
14) Males determined as inappropriate by the control doctor responsible for the test.

(III) Criteria for Subjects to be Analyzed

Males under the following criteria were excluded from the subjects to be analyzed.
1) Males markedly observed to do actions disadvantageously damaging the reliability of the examination results such as loss of diaries and records.
2) Males with difficulty in coming to hospital due to inconveniences from the side of the males (forgetting to come to hospital, unforeseen accidents, hospitalization in no apparent relation with the test sample).
3) Males dropping out from the test via the spontaneous request made by the males (dropping out).

4) Males under the conditions for exclusion or males never complying with the restriction items as revealed after the enrollment in the test.

<Test Sample>

As a sample for the test for examining the action of decreasing human serum uric acid level to be used in the Test Example 1, a refreshing drink (Table 1) containing the residual solution from the distillation of distilled spirits from barley (A) at 7.4 w/v % and the freeze-dried product (B) of the adsorbed fraction with the synthetic adsorbent from the residual solution from the distillation of distilled spirits from barley at 13.4 w/v % was used.

TABLE 1

Composition of test sample

| | Blended amount (w/v %) |
|---|---|
| Residual solution from the distillation of distilled spirits from barley (A) | 7.4 |
| Freeze-dried product (B) of the adsorbed fraction with the synthetic adsorbent from the residual solution from the distillation of distilled spirits from barley | 13.4 |
| Honey | 15.5 |
| Galacto-oligosaccharide | 4.0 |
| Lemon juice | 0.5 |

<Items for Evaluating the Efficacy for the Action of Decreasing Human Serum Uric Acid Level>

1) Serum uric acid level 4 weeks, 8 weeks and 12 weeks after the start of the test
2) Evaluation method: Comparison with the action before the intake, using one specimen t-test. Further, the level of significance was determined at 5% on both the sides.

<Examination Items Other than Serum Uric Acid Level>

The following 5 items were additionally examined 4 weeks, 8 weeks and 12 weeks after the day of the intake.
1) Medical examinations by interview: Appropriateness as a test subject (the excluding criteria, etc.) was determined, while findings of gastric state, etc. were also observed.
2) Physical examinations: height, body weight, BMI, blood pressure, and pulse (height was measured once at the examination day prior to the test; other items were measured once every examination).
3) Laboratory examinations
(i) Hematological examinations: leukocyte count, erythrocyte count, hemoglobin, hematocrit value, platelet count Hematological biochemical examinations: Na, K, Cl, Ca, IP, total protein, BUN, serum creatinine, γ-GTP, AST, ALT, ALP, LDH, neutral fat, blood sugar during fasting, total bilirubin, albumin, A/G ratio, CRP (once at the time of the examination prior to the test).
(ii) Urine examinations: pH, sugar (quantitative), protein (quantitative), occult blood reaction, creatinine (once at the time of the examination prior to the test)

Blood volume collected per examination day was about 15 ml per male per time, which totally amounted to about 75 mL.

Urine volume collected per examination day was about 10 mL per male per time, which totally amounted to about 50 mL.

(iii) Diaries and records: intake or no intake of the test sample (during the intake period alone), change of body conditions, and intake status of drugs were identified for use in determining adverse events. (Recorded items: joint pain<only at the pre-observation period>, intake or no intake of the test sample, intake habit of purine-containing foods, alcohol drinking habit, subjective symptoms and drug intake status)
5) Diet questionnaires: diets were recorded for 3 consecutive days before the examination day, to confirm no change of the amount of ingested purine throughout the test period.

<Test Subjects and Method for Incorporating Sample>

22 males of age 21 years old to 62 years old were test subjects, who satisfied the criteria (I) and (II) in the column (11 males in the normal borderline zone and 11 males in the borderline zone with mild symptoms) to ingest 25 ml of the refreshing drink in Table 1 per day for 12 weeks. No joint pain occurred in these 22 males during the observation period (about 2 weeks) prior to the test. Since the subjects to be analyzed for evaluating the test were limited to those satisfying the criterion (III) under the doctor's control, one male after enrollment (ID-09 in the borderline zone with mild symptoms) did not obey the compliance rule as test subjects that all the subjects should lead routine daily life, but changed his daily drink level from one can of foaming beer to one can of beer together with one drink of distilled spirits since the week 9 so that the daily alcohol intake increased to 2 fold or more and the purine intake increased to 1.6 fold. Hence, the male was excluded. In other words, the efficacy on the action of decreasing human serum uric acid level was analyzed in 21 of the males (41.5±13.8 years old, 11 in the normal borderline zone and 10 in the borderline zone with mild symptoms).

<Results of the Evaluation of the Efficacy on the Action of Decreasing Serum Uric Acid Level>

Prior to the evaluation of the action of decreasing serum uric acid level, first, purine intake of the subjects per day during the test period was determined so as to examine the influence of diets on the test system.

As shown in Table 2, the diet survey for 3 days prior to the examination day showed that no significant difference was observed in the amount of daily purine intake in the subjects between the start of the test (320.22±103.13 mg) and 4 weeks, 8 weeks and 12 weeks after the start of the test. Specifically, it was revealed that the purine intake in the 21 subjects to be analyzed for evaluating the efficacy on the action of decreasing serum uric acid level as described below, prior to the test and throughout the test period never varied. In other words, it was verified that no problem existed in carrying out the analysis of the test.

4 weeks, 8 weeks and 12 weeks after the start of the intake of the test sample, the serum uric acid levels in the 21 subjects as the subjects to be analyzed for evaluating the efficacy were significantly decreased 4 weeks (decreased by 0.28 mg/dL), 8 weeks (decreased by 0.52 mg/dL) and 12 weeks (decreased by 0.47 mg/dL) after the start of the intake, compared with the level at the test start (6.98±0.13 mg/dL), as shown in Table 4. Despite the preliminary serum uric acid levels, the uric acid levels in both the group of the test subjects in the normal borderline zone and the group of the test subjects in the borderline zone with mild symptoms were decreased by about 0.5 mg/dL on average, compared with the level at the test start. Hence, it was confirmed that the action of decreasing serum uric acid level with the test sample used in the test had a prophylactic and curing effect on diseases requiring the decrease of serum uric acid level.

In other words, it was indicated that the composition containing the residual solution from the distillation of distilled spirits from barley and the adsorbed fraction with the synthetic adsorbent from the residue from the distillation of distilled spirits from barley had the action of decreasing human serum uric acid level and that the action of decreasing human serum uric acid level showed a prophylactic and curing effect on diseases requiring the decrease of serum uric acid level. Additionally, the effect was exerted not temporarily but continuously throughout the intake period of the composition containing the residual solution from the distillation of distilled spirits from barley and the adsorbed fraction with the synthetic adsorbent from the residue from the distillation of distilled spirits from barley.

tion), hematological examination items, urine examination items
2) Method for evaluation: comparison of examination values with those prior to the intake, using one specimen t-test other than the determinations made by the testing doctor. The level of significance was determined at 5% on both the sides.

TABLE 2

Change of the amount of daily purine intake (questionnaire record during 3 days before the examination)

| | | Start of test | Variation | | |
|---|---|---|---|---|---|
| | | | 4 weeks | 8 weeks | 12 weeks |
| Total | n = 21 | 320.22 ± 103.13 | −9.67 ± 114.73 | −3.81 ± 89.12 | −14.76 ± 82.34 |
| Normal borderline zone | n = 11 | 306.77 ± 110.66 | −25.01 ± 98.88 | 9.94 ± 113.17 | −27.93 ± 97.92 |
| Borderline zone with mild symptoms | n = 10 | 335.02 ± 97.79 | 7.20 ± 133.35 | −18.92 ± 54.19 | −0.27 ± 63.00 |

\* Normal borderline zone: subjects of serum uric acid levels of 6.0 or more to less than 7.0 mg/dL at the examination prior to the test and at the examination at the start of the test
\* Borderline zone with mild symptoms: subjects of serum uric acid levels of 7.0 or more to less than 8.0 mg/dL at the examination prior to the test and at the examination at the start of the test
Unit: mg
Mean ± standard deviation;
\*$p < 0.05$,
\*\*$p < 0.01$ (one specimen t-test)

TABLE 3

Change of serum uric acid level

| | | | Examination day | | | | |
|---|---|---|---|---|---|---|---|
| | | | Prior to the test | Test start day | 4 weeks later | 8 weeks later | 12 weeks later |
| Total | n = 21 | Mean | 6.92 ± 0.13 | 6.98 ± 0.13 | 6.70 ± 0.14 | 6.46 ± 0.17 | 6.51 ± 0.20 |
| | | Variation | | | −0.28 | −0.52 | −0.47 |
| | | P value | | | 0.016* | 0.003** | 0.017* |
| Normal borderline zone | n = 11 | Mean Variation | 6.45 ± 0.08 | 6.47 ± 0.07 | 6.35 ± 0.13 −0.13 | 6.13 ± 0.18 −0.35 | 6.19 ± 0.18 −0.28 |
| Borderline zone with mild symptoms | n = 10 | Mean variation | 7.45 ± 0.10 | 7.54 ± 0.07 | 7.09 ± 0.20 −0.45 | 6.83 ± 0.25 −0.71 | 6.87 ± 0.34 −0.67 |

Mean: mean ± standard deviation
\*$p < 0.05$
\*\*$p < 0.01$ (one specimen t-test)

EXAMPLE 3

Test Example 2

Test for Evaluating Safety Profiles

The residual solution from distillation of distilled spirits from barley (A) and the freeze-dried product (B) of the adsorbed fraction as obtained in Example 1 were subjected to the following test for evaluating the safety profiles, for the evaluation of the safety profiles at intake.
<Test Subjects>
The subjects were selected according to those described.
<Test Sample>
As the sample for the test for evaluating the safety profiles for use in the Test Example 2, the refreshing drink (Table 1) described was used.
<Items for Evaluating the Safety Profiles>
1) Presence or absence of the relation between adverse events and the test sample, physical examinations, hematological biochemical examination items (liver function, renal func- <Examination Items as Markers for Evaluating the Safety Profiles>

The examination items are the examination items described.
<Test Subjects and Method for Ingesting the Test Sample>

The safety profiles were evaluated in 22 males (11 males in the normal borderline zone and 11 males in the borderline zone with mild symptoms) of age 21 years old to 62 years old, who satisfied the criteria (I) and (II) and took 25 mL of the refreshing drink in Table 1 per day for 12 weeks.

<Results of the Evaluation of the Test of the Safety Profiles>
(1) Adverse Events As shown in Table 5, no adverse event determined as the "presence" or "possible presence" or "possible absence" of the relation with the test sample was found. Numbness of the thumb of the right toes (ID-02), the variations of the laboratory examination values 12 weeks later (K value, Ca value, P value, ID-18) and γGTP increase (ID-5506) and cold (ID.5516) were observed in the individual males, but the testing doctor determined the absence of the relation with the test sample.

TABLE 4

Adverse events

| ID | Symptoms and comments |
|---|---|
| 02 | Numbness of the thumb of right toes, which was also observed prior to the start of the test, so that it was determined that no relation existed with the test food. |
| 18 | Increase of K value, Ca value, and P value was found 12-weeks intake later, involving hemolysis. No symptom observed. It was considered that the sample was handled erroneously before the examination, so no relation with the test food was indicated. |
| 5506 | γGTP increase. Because the alcohol drinking increased during the intake, the influence of the alcohol may possibly be emerging. Although the subject was not yet recovered, no relation with the test food was suggested. |
| 5516 | Mild fever due to cold and nose runs. No relation with the test sample. |

(2) Physical Examinations

As shown in Table 6, significant decrease of the body weight 4 weeks later and 8 weeks later (69.49±9.64 kg before the intake, the variations at −0.70 and −0.61 kg in this order) and BMI (24.35±3.38 before the intake, the variations at −0.24 and −0.22 kg/m² in this order) were observed on comparison with those values at the test start. However, no significance was observed from the values 12 weeks after the intake. There was no problematic decrease. Additionally, no change was observed in blood pressure and pulse.

(3) Hematological Biochemical Examinations

1) Examinations of Liver and Bile Duct Functions (Table 7)

Significant changes from those at the test start were observed in the increase of A/G ratio 4 weeks and 12 weeks later (1.637±0.169 before the intake, the variations were 0.055 and 0.048 in this order), AST (GOT) decrease 4 weeks later (25.3±7.5 U/L before the intake, the variation was −2.5 U/L), ALP decrease 4 weeks, 8 weeks and 12 weeks later (243.6±68.0 U/L before the intake, the variations were −13.6, −16.9 and −16.5 U/L in this order), and total bilirubin increase 4 weeks later (0.62±0.25 mg/dL before the intake, the variation was 0.14 mg/dL). All the variations were within the variations of the standard values. Therefore, no problem was indicated.

2) Examinations of Renal Functions (Table 8)

Compared with the values at the test start, significant decrease of urea nitrogen was observed 12 weeks later (14.51±2.25 mg/dL at the test start, the variation was −1.22 mg/dL). However, the variation was within the variation of the standard value, with no problem.

3) Lipid metabolism (Table 9)

During the pre-observation period and throughout the 12-week period of the intake, no significant change of neutral fat was observed.

4) Sugar Metabolism (Table 10)

During the pre-observation period and throughout the 12-week period of the intake, no significant change of blood glucose during fasting was observed.

5) Electrolytes and Trace Metals (Table 11)

As significant changes from the test start, sodium decrease 8 weeks later (143.3±1.7 mEq/L at the test start, the variation at −1.0 mEq/L), calcium decrease 12 weeks later (9.28±0.30 mg/dL at the test start, the variation at −0.30 mg/dL), and inorganic phosphorus decrease 8 weeks later (3.56±0.74 mg/dL at the test start, the variation at −0.34 mg/dL) were found. However, these were all very small variations, with no problem.

TABLE 5

Results of physical examinations

| Items | unit | Standard value | Test start | 4 weeks later | | 8 weeks later | | 12 weeks later |
|---|---|---|---|---|---|---|---|---|
| Body weight | Kg | | 69.49 ± 9.64 | 68.79 ± 9.33 | ** | 68.88 ± 9.14 | * | 69.29 ± 9.53 |
| BMI | | | 24.35 ± 3.38 | 24.11 ± 3.27 | ** | 24.13 ± 3.19 | * | 24.28 ± 3.30 |
| Systolic pressure | mmHg | Less than 140 | 122.50 ± 11.97 | 122.64 ± 14.29 | | 122.27 ± 12.61 | | 124.95 ± 14.93 |
| Diastolic pressure | mmHg | Less than 90 | 72.86 ± 10.15 | 72.91 ± 9.03 | | 74.23 ± 10.91 | | 75.68 ± 9.98 |
| Pulse | Counts/min | | 75.68 ± 8.65 | 75.41 ± 7.01 | | 76.68 ± 11.58 | | 76.45 ± 9.41 |

Mean ± standard deviation,

* p < 0.05,

** p < 0.01 (one specimen t-test)

TABLE 6

Laboratory examination values (examinations for liver and bile duct functions)

| Items | Unit | Standard value | Test start | 4 weeks later | | 8 weeks later | | 12 weeks later | |
|---|---|---|---|---|---|---|---|---|---|
| Total protein | g/dL | 6.5-8.2 | 7.39 ± 0.31 | 7.35 ± 0.30 | | 7.32 ± 0.35 | | 7.31 ± 0.37 | |
| Albumin | g/dL | 3.7-5.5 | 4.55 ± 0.20 | 4.62 ± 0.27 | | 4.47 ± 0.24 | | 4.54 ± 0.28 | |
| A/G ratio | | 1.30-2.00 | 1.637 ± 0.169 | 1.692 ± 0.180 | * | 1.610 ± 0.200 | | 1.685 ± 0.180 | * |
| AST (GOT) | U/L | 10-40 | 25.3 ± 7.5 | 22.8 ± 5.2 | | 25.0 ± 8.7 | | 24.2 ± 5.5 | |
| ALT (GPT) | U/L | 5-45 | 27.6 ± 19.2 | 26.3 ± 16.9 | | 29.5 ± 22.2 | | 26.7 ± 16.7 | |
| LDH | U/L | 120-245 | 199.1 ± 33.7 | 200.6 ± 28.2 | | 204.0 ± 43.1 | | 191.6 ± 29.8 | |
| ALP | U/L | 104-338 | 243.6 ± 68.0 | 230.0 ± 63.7 | * | 226.7 ± 67.0 | * | 227.2 ± 68.6 | * |
| γGTP | U/L | 79 or less | 46.5 ± 42.1 | 46.4 ± 36.9 | | 48.9 ± 46.7 | | 53.0 ± 57.6 | |
| Total bilirubin | mg/dL | 0.2-1.0 | 0.62 ± 0.25 | 0.76 ± 0.24 | * | 0.69 ± 0.24 | | 0.65 ± 0.26 | |

Mean ± standard deviation,
* $p < 0.05$,
** $p < 0.01$ (one specimen t-test)

TABLE 7

Laboratory examination values (examinations of renal functions)

| Items | Unit | Standard value | Test start | 4 weeks later | 8 weeks later | 12 weeks later | |
|---|---|---|---|---|---|---|---|
| Creatinine | mg/dL | 0.65-1.09 | 0.868 ± 0.128 | 0.870 ± 0.125 | 0.858 ± 0.117 | 0.860 ± 0.119 | |
| Urea nitrogen | mg/dL | 8.0-20.0 | 14.51 ± 2.25 | 13.98 ± 2.82 | 14.12 ± 2.47 | 13.29 ± 1.90 | * |

Mean ± standard deviation,
* $p < 0.05$,
** $p < 0.01$ (one specimen t-test)

TABLE 8

Laboratory examination values (lipid metabolism)

| Items | Unit | Standard value | Test start | 4 weeks later | 8 weeks later | 12 weeks later |
|---|---|---|---|---|---|---|
| Neutral fat | mg/dL | 50-149 | 122.9 ± 86.5 | 141.1 ± 74.5 | 151.4 ± 108.9 | 133.8 ± 84.1 |

Mean ± standard deviation,
* $p < 0.05$,
** $p < 0.01$ (one specimen t-test)

TABLE 9

Laboratory examination values (glucose metabolism)

| Item | Unit | Standard value | Test start | 4 weeks later | 8 weeks later | 12 weeks later |
|---|---|---|---|---|---|---|
| Blood glucose during fasting | mg/dL | 70-109 | 91.7 ± 9.4 | 92.5 ± 9.6 | 94.5 ± 10.0 | 93.5 ± 8.2 |

Mean ± standard deviation,
* $p < 0.05$,
** $p < 0.01$ (one specimen t-test)

TABLE 10

Laboratory examination values (electrolytes and trace metals)

| Items | Unit | Standard value | Test start | 4 weeks later | 8 weeks later | | 12 weeks later | |
|---|---|---|---|---|---|---|---|---|
| Sodium | mEq/L | 135-145 | 14.3.3 ± 1.7 | 142.4 ± 1.3 | 142.2 ± 1.5 | * | 142.6 ± 1.4 | |
| Potassium | mEq/L | 3.5-5.0 | 3.97 ± 0.28 | 3.90 ± 0.24 | 3.88 ± 0.34 | | 4.07 ± 1.25 | * |
| Chlorine | mEq/L | 98-108 | 101.3 ± 2.1 | 101.4 ± 2.0 | 100.2 ± 3.3 | | 101.0 ± 2.7 | |
| Calcium | mg/dL | 8.2-10.0 | 9.28 ± 0.30 | 9.25 ± 0.25 | 9.18 ± 0.45 | | 8.98 ± 0.45 | |
| Inorganic Phosphorus | mg/dL | 2.5-4.5 | 3.56 ± 0.74 | 3.28 ± 0.53 | 3.23 ± 0.59 | | 4.07 ± 3.06 | |

Mean ± standard deviation,
* $p < 0.05$,
** $p < 0.01$ (one specimen t-test)

(4) Hematological Examinations

As shown in Table 12, significant decrease of MCH (mean corpuscular hemoglobin) 4 weeks and 8 weeks later (31.05±1.06 pg at the test start, the variations at −0.49 pg and −0.28 pg in this order), significant increase of MCV (mean corpuscular volume) 12 weeks later (94.7±3.9 pg at the test start, the variation at 1.7 pg), and significant decrease of MCHC (mean corpuscular hemoglobin concentration) 8 weeks and 12 weeks later (32.81±0.66% at the test start, the variations at −0.41%, −0.53%, and −0.79% in this order) were observed, compared with those values at the test start. Additionally, significant increase of platelet counts 4 weeks later (241,700±48,900 platelet counts/μl, variation at 10,600 platelet counts/μL) was observed. However, the platelet count was decreased 8 weeks and 12 weeks later, so the variations were within the physiological range.

TABLE 11

Laboratory examination values (Hematological examinations)

| Items | Unit | Standard value | Test start day | 4 weeks late | | 8 weeks later | | 12 weeks later | |
|---|---|---|---|---|---|---|---|---|---|
| Leukocyte count | /μL | 3500-9700 | 5563.6 ± 1767.7 | 5618.2 ± 1470.8 | | 5753.6 ± 1621.8 | | 6089.1 ± 2183.7 | |
| Erythrocyte count | ×10,000/μL | 438-577 | 491.3 ± 34.8 | 494.5 ± 36.8 | | 494.9 ± 40.0 | | 490.5 ± 40.0 | |
| Hemoglobin | g/dL | 13.6-18.3 | 15.24 ± 0.98 | 15.10 ± 1.07 | | 15.21 ± 1.22 | | 15.15 ± 1.01 | |
| hematocrit | % | 40.4-51.9 | 46.46 ± 3.11 | 46.61 ± 3.33 | | 47.16 ± 4.29 | | 47.37 ± 3.82 | |
| MCV | fL | 83-101 | 94.7 ± 3.9 | 94.5 ± 4.1 | | 95.4 ± 4.3 | | 96.4 ± 4.9 | * |
| MCH | pg | 28.2-34.7 | 31.05 ± 1.06 | 30.55 ± 1.14 | ** | 30.76 ± 1.14 | * | 30.82 ± 1.22 | |
| MCHC | % | 31.8-36.4 | 32.81 ± 0.66 | 32.40 ± 0.70 | ** | 32.28 ± 0.70 | ** | 32.03 ± 1.22 | ** |
| Platelet count | ×10,000/μL | 14.0-37.9 | 24.17 ± 4.89 | 25.23 ± 4.92 | ** | 24.13 ± 5.38 | | 24.11 ± 5.06 | |

Mean ± standard deviation,
* $p < 0.05$,
** $p < 0.01$ (one specimen t-test)

(5) Urine Examinations (Table 13, Table 14)

No change of glucose (qualitative) or pH was observed.

TABLE 12

Laboratory examination values (urine examination No. 1)

| Items | Standard value | Test start | 4 weeks later | 8 weeks later | 12 weeks later |
|---|---|---|---|---|---|
| Glucose (qualitative) | (−) (+) | (−) 22 males | (−) 22 males | (−) 22 males | (−) 22 males |
| pH | 4.8-7.5 | 5.66 ± 0.76 | 5.89 ± 0.80 | 5.84 ± 0.86 | 5.75 ± 0.65 |

Mean ± standard deviation,
* $p < 0.05$,
** $p < 0.01$ (one specimen, t-test)

TABLE 13

Laboratory examination values (urine examination No. 2)

|  |  |  |  | 4 weeks later | | | 8 weeks later | | | 12 weeks later | | |
|---|---|---|---|---|---|---|---|---|---|---|---|---|
|  |  | Standard value |  | − | ± | + | − | ± | + | − | ± | + |
| Urine protein | (−) (±) | Test start day | − | 2 2 | 0 | 0 | 2 0 | 2 | 0 | 2 1 | 0 | 1 |
| Occult blood test | (−) | Test start day | − | 2 2 | 0 | 0 | 2 1 | 1 | 0 | 2 2 | 0 | 0 |

As described above, adverse events, the results of the physical examinations, the hematological biochemical examinations, the hematological examinations, and the urine examinations, and the like were evaluated in the subjects having ingested the test sample for 12 weeks under the doctor's control. No problem was found in the safety profiles including all of the subjective and objective symptoms, the results by the doctor's interview, and the results of the physical examinations and the laboratory examination values, within the test.

EXAMPLE 4

Prescription examples of the composition according to the invention are now described below.

PRESCRIPTION EXAMPLE 1

Production of Refreshing Drink Using the adsorbed fraction with the synthetic adsorbent from the residue from distillation of distilled spirits from barley as obtained in Example 1, a refreshing drink of the following composition was produced according to a routine method.

| | |
|---|---|
| Residual solution from distillation of distilled spirits from barley | 7.4 w/v % |
| Adsorbed fraction with the synthetic adsorbent from the residue from the distillation of distilled spirits from barley | 13.4 w/v % |
| Honey | 15.5 w/v % |
| Galacto-oligosaccharide | 4.0 w/v % |
| Lemon juice | 0.5 w/v % |

PRESCRIPTION EXAMPLE 2

Production of Fruit Juice Drink
Using the adsorbed fraction with the synthetic adsorbent from the residue from distillation of distilled spirits from barley as obtained in Example 1, a fruit juice drink of the following composition was produced according to a routine method.

| | |
|---|---|
| Adsorbed fraction with the synthetic adsorbent from the residue from distillation of distilled spirits from barley | 5.0 w/v % |
| Residual solution from distillation of distilled spirits from barley | 8.0 w/v % |
| Blueberry juice | 21.6 w/v % |
| Glucose | 5.0 w/v % |
| Galacto-oligosaccharide | 5.0 w/v % |
| Honey | 3.2 w/v % |

PRESCRIPTION EXAMPLE 3

Production of Tablet
Using the adsorbed fraction with the synthetic adsorbent from the residue from distillation of distilled spirits from barley as obtained in Example 1, a tablet of the following composition was produced according to a routine method.

| | |
|---|---|
| Residue from distillation of distilled spirits from barley | 5.0 w/v % |
| Adsorbed fraction with the synthetic adsorbent from the residue from distillation of distilled spirits from barley | 10.0 w/v % |
| Fermented barley fiber (manufactured by Barley Fermentation Technologies, Inc., O-ita) | 15.0 w/v % |
| Crystalline cellulose | 55.0 w/v % |
| Sucrose fatty acid ester | 10.0 w/v % |
| Dextrin | 5.0 w/v % |

As apparently shown in the results of the Test Example 1 and the Test Example 2, thus, the composition obtained from the component from barley subjected to fermentation and the residue from distillation of distilled spirits from barley has an action of decreasing human serum uric acid level throughout the intake period on one to 10 g per day. It was shown that even when the composition was orally given, the composition was a highly safe material.

INDUSTRIAL APPLICABILITY

The composition of the invention utilizes the action of decreasing serum uric acid level as derived from the active ingredient from the fermentation of barley as a plant of the family Gramineae having been familiar as a very healthy food, which is a cereal indispensable for humans since the dawn of history and is described in traditional Japanese medical books. Hence, the composition is at a high applicability as a functional food.

Additionally, the composition of the invention is derived from the material having been ingested greatly and is highly safe when ingested, so that the composition is at a high applicability in terms of a small risk of adverse actions.

Furthermore, the resource never used traditionally is used for the composition of the invention, so the invention is at a high applicability in view of the production of highly valuable merchandises at low cost.

The invention claimed is:
1. A composition consisting essentially of a component from barley which has been subjected to alcohol fermentation using *Aspergillus kawachii* and which is a residue from a distillation of distilled spirits of the barley and wherein said component from barley is a fraction produced by ion exchange treatment using an aromatic series or methacryl series wherein the component from barley is separated into a solid fraction and a liquid fraction and wherein the liquid fraction is separated out by the ion exchange treatment and wherein said liquid fraction contains the component from barley which decreases a serum uric acid level and wherein said liquid fraction contains crude proteins at 40-60% by weight, polyphenols at 7-12% by weight, polysaccharides at 5-10% by weight, and organic acids at 4-10% by weight.

* * * * *